United States Patent [19]
Goralnik et al.

[11] Patent Number: 5,964,722
[45] Date of Patent: Oct. 12, 1999

[54] CERVICAL-THORACIC BRACE

[76] Inventors: B. Scott Goralnik, 5 Pleasant Wood Way, Ormond Beach, Fla. 32174; Albert William Gillespy, 790 John Anderson Dr., Ormond Beach, Fla. 32176

[21] Appl. No.: 08/789,662

[22] Filed: Jan. 27, 1997

[51] Int. Cl.[6] .................................................. A61F 5/00
[52] U.S. Cl. ............................................................ 602/18
[58] Field of Search ........................................ 602/17–19

[56] References Cited

U.S. PATENT DOCUMENTS

| | | | |
|---|---|---|---|
| 3,364,926 | 1/1968 | Alderson | 602/18 |
| 3,724,452 | 4/1973 | Nitschke | 602/18 |
| 4,383,523 | 5/1983 | Schurman | 602/18 X |
| 4,515,153 | 5/1985 | Calabrese . | |
| 4,628,913 | 12/1986 | Lerman | 602/18 |
| 4,677,969 | 7/1987 | Calabrese . | |
| 4,827,915 | 5/1989 | Gorsen | 602/18 |
| 5,007,413 | 4/1991 | Aalvik Thune . | |
| 5,010,877 | 4/1991 | Druskoczi . | |
| 5,038,759 | 8/1991 | Morgenstern | 602/18 |
| 5,230,698 | 7/1993 | Garth | 602/18 |
| 5,242,377 | 9/1993 | Boughner et al. | 602/17 |
| 5,320,596 | 6/1994 | Catipovic et al. | 602/18 |
| 5,411,471 | 5/1995 | Terrazas | 602/18 |
| 5,437,612 | 8/1995 | Moore et al. | 602/18 |
| 5,531,669 | 7/1996 | Varnau | 602/18 |
| 5,632,722 | 5/1997 | Tweardy et al. | 602/18 |

*Primary Examiner*—Linda C.M. Dvorak
*Attorney, Agent, or Firm*—Frost & Jacobs LLP

[57] ABSTRACT

A cervical brace has a cervical anterior base (16) with an anterior distal neck-chin plate (1, 27) and a posterior-distal neck-chin plate (9, 28) that are extended over designedly wide areas of a user's shoulders (22) and joined together to provide broad-base support for an anterior-proximal neck-chin plate (2) and an inclined posterior-proximal neck-chin plate (10) with which cervical vertebrae (25) are held desirably in place from the cervical anterior base. A rigid thoracic bar (5) is extended adjustably upward from a chest plate (6) that is strapped to the user. Designedly cushioned and washable pads (3, 4, 7, 11, 12) are detachably fastened to the neck-chin plates and the chest plate. A selectively neck supporting method employs an incline action against a reciprocally inclined back of a person's head by forcing a front portion and a rear portion of the cervical anterior base together to provide a highly weight-supportive base on a broad portion of the person's shoulder area simultaneously.

26 Claims, 3 Drawing Sheets

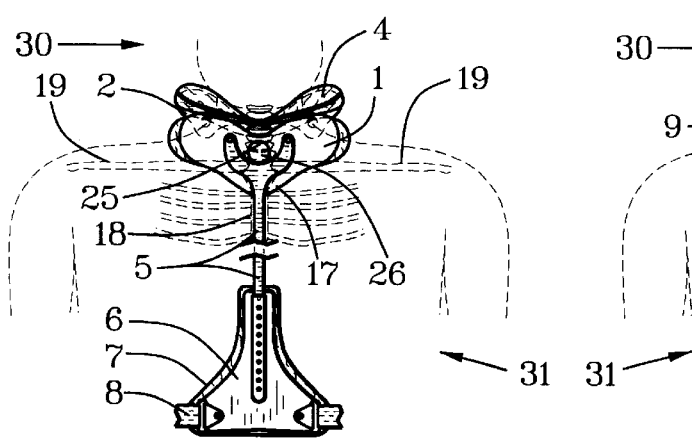
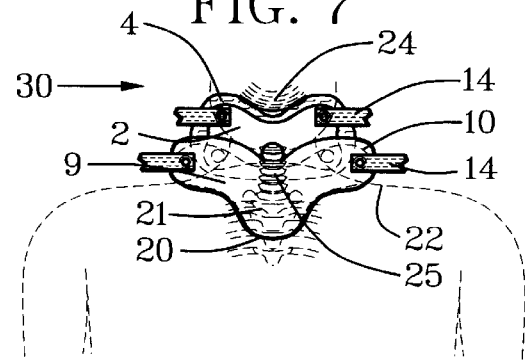
FIG. 6
FIG. 7
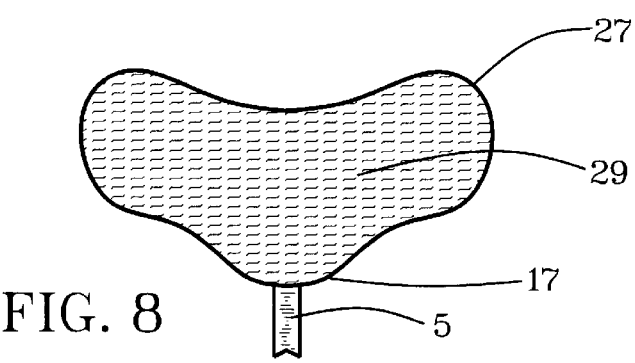
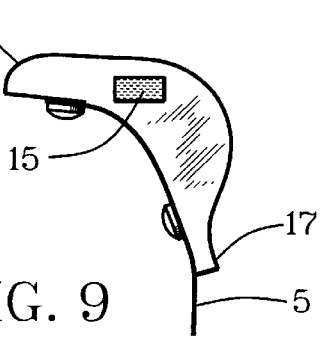
FIG. 8
FIG. 9
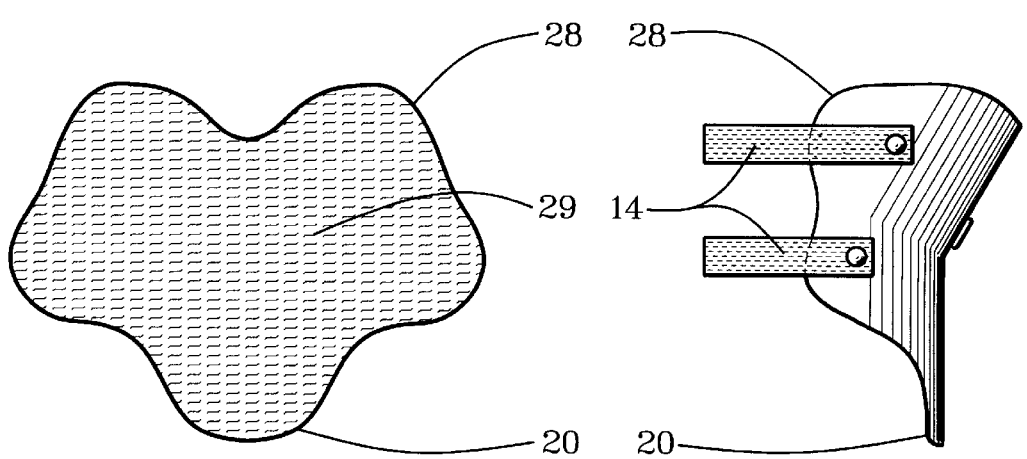
FIG. 10
FIG. 11

CERVICAL-THORACIC BRACE

BACKGROUND OF THE INVENTION

This invention relates to neck braces for selectively holding and maintaining injured cervical spine inclusive of vertebrae, discs, muscles, ligaments and nerves of people during healing convalescent time.

A wide variety of cervical restraints, collars and braces have been devised to position injured necks and heads of people properly for the healing convalescent time or permanently if necessary. None, however, have provided a complete shoulder base, adjustability of straightening means and convenience of use in manner taught by this invention.

Examples of different but related cervical supports are described in the following patent documents. U.S. Pat. No. 5,242,377, issued to Boughner, et al., taught a head brace attached to a back brace. U.S. Pat. No. 5,230,698, issued to Garth, described a two-piece front-and-back cervical collar with edges that terminated vertically on top of the clavicle. U.S. Pat. No. 5,010,877, issued to Druskoczi, taught a replaceable lining for a surgical collar. U.S. Pat. No. 5,007,413, issued to Thune, taught a double-strap supporting device. U.S. Pat. Nos. 4,515,153 and 4,677,969, issued to Calabrese, taught front-and-back stabilizer plates for a cervical collar, the latter of which had a tracheal-access orifice.

SUMMARY OF THE INVENTION

In light of need for improvement of cervical supports, objects of this invention are to provide a cervical brace which:

Rests on horizontally broad front, back and side surfaces of the clavicle in order to provide a body's maximum lifting support for selectively supporting and/or maintaining cervical vertebrae in desired relationship to thoracic vertebrae;

Eliminates edge-contact support of head and neck by small section of the clavicle in order to decrease edge-cutting action, fatigue and pain;

Provides adjustable-length neck maintenance between a broad, cushioned shoulder base and broad, cushioned bases on a head and lower jaw;

Has quick-and-easy attachment with front and back brace portions joined by hook and loop fastener straps;

Has an anterior bar that is extendible adjustably intermediate a front brace portion and a front plate that is attachable to a user's waist with a single fastener strap;

Has a posterior vertebrae section extended vertically downward from the occiput brace portion intermediate broad surfaces of contact of the back brace portion with the clavicle in order to provide anterior/posterior rigidity and moderate rigidity for selectively universal rigidity in combination with the front brace portion and the front stiffener if the front stiffener is used selectively; and Has conveniently replaceable body-contact covers which can be made of cotton that are washable and designedly cushioned for all body-contact portions.

This invention accomplishes these and other objectives with a cervical brace having a cervical support base with a thoracic plate joined together to provide broad-base support for a chin plate and an inclined head plate with which cervical vertebrae are held desirably in place. A thoracic bar is extended adjustably upward from a chest plate that is strapped to the user. Designedly cushioned and washable pads are detachably fastened to the chin plate, the posterior head plate and the chest plate. A thoracic bar employs an incline action against a reciprocally inclined back of a person's head by forcing a front portion and a rear portion of the cervical support base together to provide a highly weight-supportive base on a broad portion of the person's shoulder area simultaneously.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

This invention is described by appended claims in relation to description of a preferred embodiment with reference to the following drawings which are described briefly as follows:

FIG. 6 is a front view in relation to a clavicle, a sternum and a jaw of an individual shown in dashed lines;

FIG. 7 is a rear view in relation to top thoracic vertebrae, shoulders and occipital bone of a user shown in dashed lines;

FIG. 8 is a front view of a one-piece anterior plate;

FIG. 9 is a side view of the FIG. 8 illustration;

FIG. 10 is a rear view of a one-piece rear posterior head plate; and

FIG. 11 is a side view of the FIG. 11 illustration.

DESCRIPTION OF PREFERRED EMBODIMENT

Figure 1:
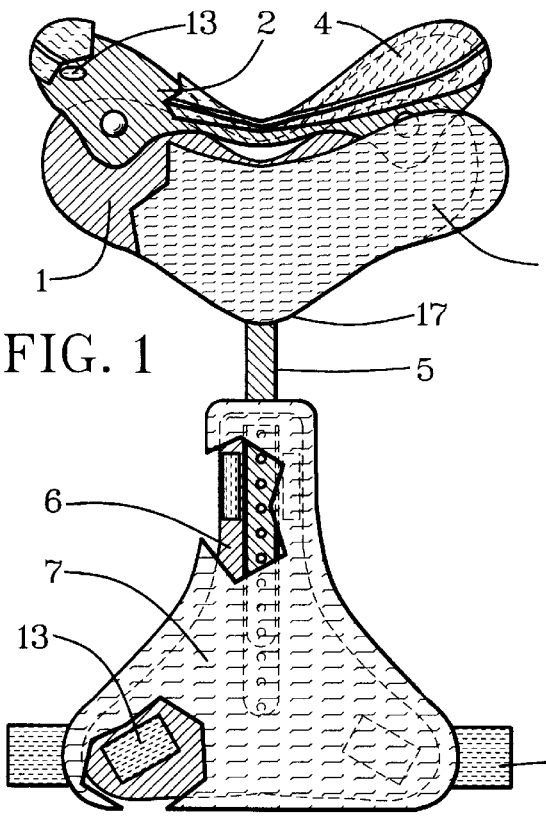
FIG. 1 is a partially cutaway rear view of an anterior chin section attached to a thoracic bar and neck/chin plate.
Figure 2:
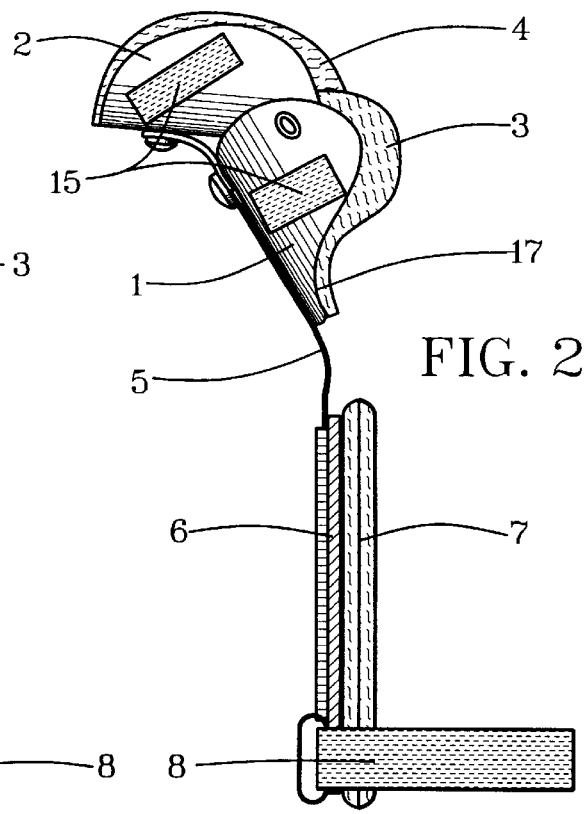
FIG. 2 is a side view of the FIG. 1 illustration.

Reference is made first to FIGS. 1-2. An anterior-distal neck-chin plate 1 is sized, shaped and contoured to fit the persons chin and jaw region. Attached to a body-contact side of the anterior-distal neck-chin plate 1 is a chin pad 3 and attached to an anterior-proximal neck-chin plate 2 is a neck-chin pad 4. The anterior-distal neck-chin pad 3 and the anterior-proximal neck-chin pad 4 are preferably cushiony, washable and attachable with hook and loop fasteners 13.

A rigid thoracic bar 5 is attached to the anterior-proximal neck-chin plate 2 and from a chest plate 6 having a chest pad 7 attached to a body-contact side of the chest plate 6 and having a thoracic strap 8 with which the chest plate 6 is attached to a user's body. The thoracic bar 5 is preferably adjustable telescopically in length intermediate the front chin plate 1 and the chest plate 6. The chest pad 7 is preferably attachable with hook and loop fasteners and the girth strap 8 is preferably fastenable with matching hook and loop straps 15.

Figure 3:
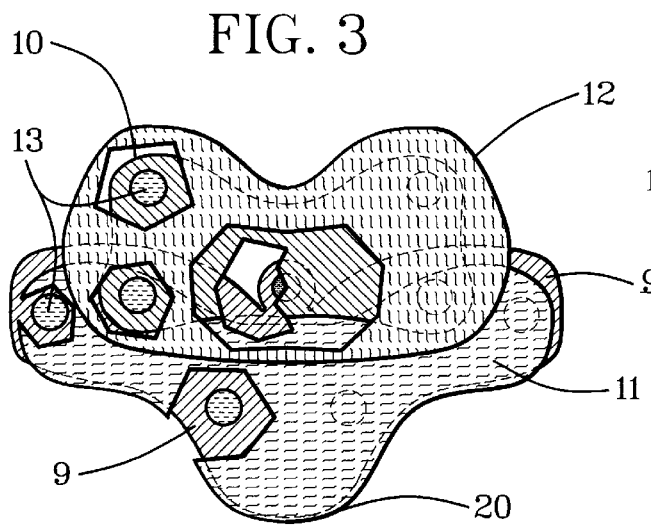
FIG. 3 is a partially cutaway front view of a posterior head plate having an attachable chin plate.
Figure 4:
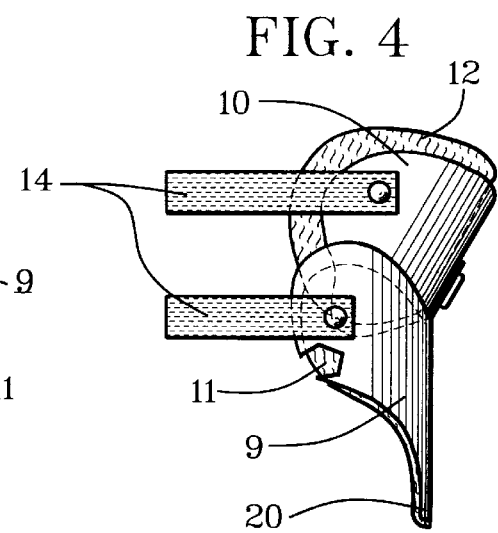
FIG. 4 is a side view of the FIG. 3 illustration.

Referring to FIGS. 3-4, a posterior-distal neck-chin plate 9 is sized, shaped and contoured to fit over top and lateral side portions of a user's neck. Extended upwardly from the posterior-distal neck-chin plate 9 is a posterior-proximal neck-chin plate 10 that is sized, shaped and contoured to fit under a designedly large portion of a back of the user's head. Attached to a body-contact side of the posterior-distal neck-chin plate 9 is a posterior-proximal neck-head pad 11 and attached to the posterior-proximal neck-chin plate 10 is a posterior-distal neck-head pad 12. The posterior-proximal neck-head pad 11 and the posterior-distal neck-head pad 12 are preferably cushiony, washable and attachable with hook and loop fasteners 13. The anterior-distal neck-chin plate 1 and the posterior-distal neck-chin plate 9 can be joined together with selective closeness and tension with hook and loop fastening plate straps 14. Similarly, the anterior-proximal neck-chin plate 2 and the posterior-proximal neck-chin plate 10 can be joined together with selective closeness and tension with separate hook and loop fastening straps 14. Preferably the straps 14 are attachable with matching hook and loop fastening material 15 in either forwardly extended relationship as shown or in rearwardly extended relationship.

Referring to FIGS. 1–7, a cervical anterior base 16 is formed by joining the anterior-distal neck-chin plate 1 and the posterior-distal neck-chin plate 9 as depicted and as described in relation to FIGS. 1–5. The anterior-distal neck-chin plate 1 has a front base 17 extending downward centrally to be positioned over a user's sternum 18 while lateral portions of the anterior-distal neck-chin plate 1 are extended laterally over the user's clavicle 19. The posterior-distal neck-chin plate 9 has a back base 20 extending downward centrally to be positioned over a user's top thoracic vertebrae 21 while lateral portions of the posterior-distal neck-chin plate 9 are extended laterally over top and rear portions of the user's shoulders 22.

Spread out over shoulders 22, sternum 18, clavicle 19 and top thoracic vertebrae 21, the cervical anterior base 16 is supported by the greatest weight-supportive portion of a normal person's body. With an anterior-proximal neck-chin plate 2 positioned under a mandible 23 and with a posterior-proximal neck-chin plate 10 inclined against a normally inclined occipital bone 24, inward force of the anterior-distal neck-chin plate 1 in combination with the anterior-proximal neck-chin plate 2 and the posterior-distal neck-chin plate 9 in combination with the posterior-proximal neck-chin plate 10 can provide greater neck support. Further, fatigue and pain from selective support of the neck in this manner is low because of the broad surface area of the cervical anterior base 16. This allows designedly long periods of selective neck supports while cervical vertebrae 25 have a chance to heal and to mend before assuming normal head weight and motion.

Conventionally in prior art, neck braces have had vertical edges positioned on small portions of the clavicle 19 to provide a linear binding or wrapping effect like a cast.

Occasionally there are tracheal injuries or the requirement of a tracheostomy associated with cervical injuries and dysfunctions. To accommodate this, a tracheal-access orifice 26 can be provided in the anterior-distal neck-chin plate 1 as illustrated in FIG. 6.

Referring to FIGS. 8–11, a one-piece anterior head plate 27 and a one-piece posterior head plate 28 can be employed as a design option to the multiple-plate construction illustrated in FIGS. 1–7. The same features can be single-piece molded instead of plurality-piece attached as depicted in FIGS. 8–11. As depicted for single-piece construction, a similarly sized, shaped and anterior-proximal neck-chin head plate 2 is extended designedly upward and forward from a one-piece anterior head plate 27 having also a similarly contoured front base 17. Likewise, a similarly sized, shaped and posterior-proximal neck-chin plate 10 is extended designedly upward and rearward from a posterior head plate 28 having also a similarly contoured back base 20. Further, a one-piece anterior head plate 27 and a posterior head plate 28 can have cushioned body-contact surfaces 29 built onto them if desired. Replacement pads are provided for keeping them clean and dry.

Figure 5:
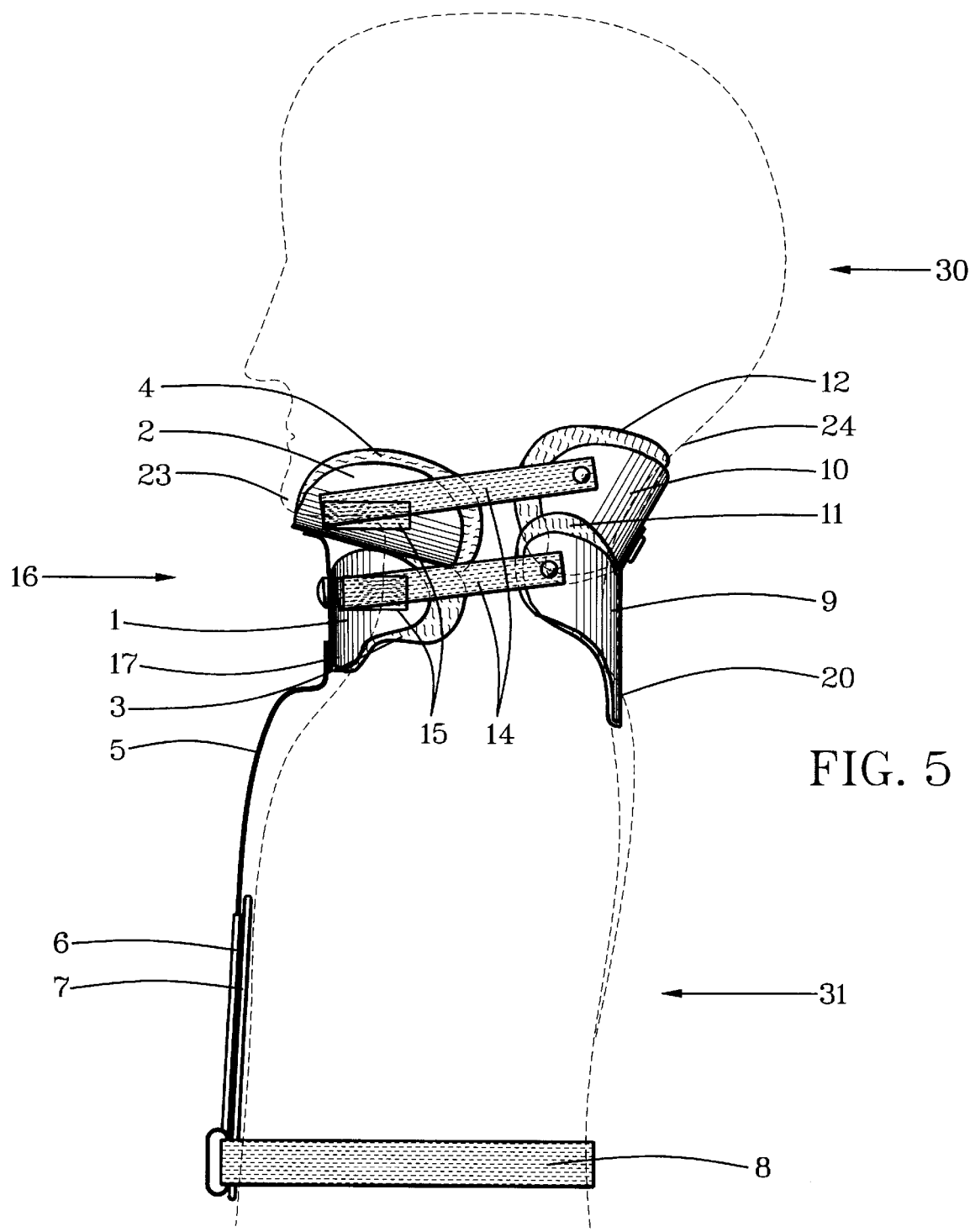
FIG. 5 is a side elevation view of a cervical anterior base positioned on an individual represented in dashed lines.

Referring summarily to FIGS. 1–11, this invention teaches and makes possible selective support of a person's neck or cervical vertebrae 25 and related bone and/or soft tissue as follows. A one-piece anterior head plate 27 or a combined anterior adjustable neck-chin plate 1 and anterior-posterior neck-chin plate 2, either having a front base 17, is positioned over a broad portion of a person's sternum 18 and clavicle 19. A one-piece posterior head plate 28 or a combined posterior-distal neck-chin plate 9 and posterior-proximal neck-chin plate 10, either having a back base 20, is positioned over a broad portion of a person's shoulders 22 and top thoracic vertebrae 21. This forms a cervical anterior base 16 having a front portion and a rear portion relative to the person's head 30 and torso 31 as depicted in FIGS. 5–7.

The front portion and the rear portion of the cervical anterior base 16 are then forced together for selective neck support or held. Neck support is achieved by an incline action of an inclined one-piece posterior head plate 28 or a combined posterior-distal neck-chin plate 9 and posterior-proximal neck-chin plate 10. A seat for the cervical anterior base 16 is provided by person's shoulders 22, top thoracic vertebrae 21, sternum 18 and a broad portion of the clavicle 19. Inward force assures a load-bearing seat and simultaneously operates incline action of the rear portion of the cervical support base 16 on a reciprocally or matching incline of the occipital bone 24.

Inward force of the front and rear portions of the cervical anterior base 16 can be provided by such simple and inexpensive means as hand-pressuring and then fastening with plate straps 14 onto matching hook and loop fastening straps 15 or by use of such other belt-tightening or strap-tightening means as desired.

The rigid thoracic bar 5 and chest plate 6 are employed by positioning the chest plate comfortably on a user's chest in relation to body size and shape and in relation to breasts of female users. Length of the rigid thoracic bar 5 is adjusted and set accordingly with the thoracic strap 8 adjusted for comfort and fastened. The chest plate 6 and rigid thoracic bar 5 will not fall down on a user's torso 31 without shoulder straps because of shoulder-base contact of selected plates 1, 9, 27 and 28 in a fastened mode of the cervical anterior base 16.

A new and useful cervical brace having been described, all such foreseeable modifications, adaptations, substitutions of equivalents, mathematical possibilities of combinations of parts, pluralities of parts, applications and forms thereof as described by the following claims and not precluded by prior art are included in this invention.

What is claimed is:

1. A cervical-thoracic brace consisting essentially of:
   a cervical anterior base having an anterior neck plate and a posterior neck plate;
   the anterior neck plate being sized, shaped and contoured to extend laterally over top portions of a user's chest proximate a top portion of the sternum and lateral portions of the clavicle;
   the anterior neck plate having a front base extended downward from a central portion of the anterior neck plate adapted to be positioned vertically over a portion of the user's sternum and clavicle;
   the posterior neck plate being sized, shaped and contoured to extend laterally over portions of opposite-side top and rear areas of the user's neck and having a back base extended downward from a central portion of the posterior neck plate adapted to be positioned vertically over a portion of the user's upper thoracic vertebrae;

a chin plate extended upward and forward from the anterior neck plate;

the chin plate being sized, shaped and contoured to support the user's head from proximately under the user's mandible;

a head plate extended upward and rearward from the rear neck plate;

the head plate being sized, shaped and contoured to support the user's head from proximately under the user's occipital bone;

fastener means with which the anterior neck plate and the posterior neck plate are fastened together;

a chest plate that is adapted to be positioned on the user;

at least one thoracic strap to attach the chest plate to the user; and a rigid thoracic bar extended upwardly from the chest plate, the rigid thoracic bar being extended intermediate the chest plate and the anterior neck plate.

2. A cervical-thoracic brace as described in claim 1 wherein:

the rigid thoracic bar is adjustable in length of extension intermediate the chest plate and the anterior neck.

3. A cervical-thoracic brace as described in claim 1 wherein:

a bottom portion of the rigid thoracic bar is positioned in a bar pocket from which the rigid thoracic bar is extendible telescopically for adjustable-length positioning intermediate the chest plate and the anterior neck plate; and a fastener with fastener attachment of the bottom portion of the rigid thoracic bar to the chest plate.

4. A cervical-thoracic brace as described in claim 3 wherein:

the anterior neck plate has a trachea-access orifice that is positioned centrally intermediate opposite lateral ends of the anterior neck plate.

5. A cervical-thoracic brace as described in claim 4 wherein:

a top portion of the rigid thoracic bar has a trachea-orifice bay intermediate positions of attachment of the top portion of the rigid thoracic bar to the anterior neck plate.

6. A cervical-thoracic brace as described in claim 1 wherein:

the anterior neck plate has a trachea-access orifice that is positioned centrally intermediate opposite lateral ends of the anterior neck plate.

7. A cervical-thoracic brace as described in claim 1 wherein:

the chin plate is separate from and attachable to the anterior neck plate.

8. A cervical-thoracic brace as described in claim 1 wherein:

the chin plate and the anterior neck plate are a one-piece construction.

9. A cervical-thoracic brace as described in claim 1 wherein:

the head plate and the posterior neck plate are a one-piece construction.

10. A cervical-thoracic brace as described in claim 9 wherein:

the chin plate and the anterior neck plate are a one-piece construction.

11. A cervical-thoracic brace as described in claim 1 wherein:

the head plate is separate from and attachable to the posterior neck plate.

12. A cervical-thoracic brace as described in claim 11 wherein:

the chin plate and the anterior neck plate are a one-piece construction.

13. A cervical-thoracic brace as described in claim 11 wherein:

the chin plate is separate from and attachable to the anterior neck plate.

14. A cervical-thoracic brace, as described in claim 1 wherein:

at least a portion of the body-contact sides of the anterior neck plate, the posterior neck plate and the chin plate are covered with cushioned pads.

15. A cervical-thoracic brace as described in claim 14 wherein:

the cushioned pads are attached to the body-contact sides of the anterior neck plate, the posterior neck plate and the chin plate with detachable means.

16. A cervical-thoracic brace as described in claim 15 wherein:

the detachable means are straps using hook and loop fastening material.

17. A cervical-thoracic brace as described in claim 16 wherein:

the cushioned pads are washable material.

18. A cervical-thoracic brace as described in claim 1 wherein:

at least a portion of a body—contact side of the chest plate is covered with a cushioned pad; and further wherein the rigid thoracic bar extends intermediate the chest plate and the anterior neck plate.

19. A cervical-thoracic brace as described in claim 18 wherein:

the cushioned pad is attached to the body-contact side of the chest plate with detachable means.

20. A cervical-thoracic brace as described in claim 19 wherein:

the detachable means is hook and loop fastening material; and the cushioned pad is washable.

21. A cervical-thoracic brace consisting essentially of:

a cervical support base having anterior neck plate and a posterior neck plate;

the anterior neck plate being sized, shaped and contoured to extend laterally over top portions of a user's chest proximate a top portion of the sternum and lateral portions of the clavicle;

the posterior neck plate being sized, shaped and contoured to extend laterally over portions of opposite-side top and rear areas of the user's shoulders and having a back base extended downward from a central portion of the posterior neck plate to extend vertically over a portion of the user's upper thoracic vertebrae;

a chin plate extended upward and forward from the anterior neck plate;

the chin plate being sized, shaped and contoured to support the user's head from proximately under the user's mandible;

a head plate extended upward and rearward from the posterior neck plate;

the head plate being sized, shaped and contoured to support the user's head from proximately under the user's occipital bone;

fastener means with which the anterior neck plate and the posterior neck plate are fastened together;

a rigid thoracic bar extended upwardly from a chest plate that is adapted to be positioned on the user with at least one thoracic strap;

the rigid thoracic bar being extended intermediate the chest plate and the anterior neck plate;

a bottom portion of the rigid thoracic bar is positioned in a bar pocket from which the rigid thoracic bar is extendible telescopically for adjustable-length positioning intermediate the chest plate and the anterior neck plate;

a fastener with fastener attachment of the bottom portion of the rigid thoracic bar to the chest plate;

the chin plate is separate from and attachable to the anterior neck plate; the head plate is separate from and attachable to the posterior neck plate; and at least a portion of the body-contact sides of the anterior neck plate, the posterior plate, the chin plate and the chest plate are covered with cushioned pads.

22. A cervical-thoracic brace as described in claim 21 wherein:

the anterior neck plate and the posterior neck plate are attachable in juxtaposed positioning with hook and fastening material on strips having common contact surfaces with lengths which overlap for adjustment of closeness of the anterior neck plate and the posterior neck plate.

23. A cervical-thoracic brace as described in claim 22 wherein:

the cushioned pads are attachable to the body-contact sides of the anterior neck plate, the posterior neck plate, the chin plate and the chest plate with matching hook and loop fastening material.

24. A cervical-thoracic brace as described in claim 23 wherein:

the cushioned pads are washable.

25. A cervical-thoracic brace as described in claim 24 wherein:

the chest plate is attachable to a body of the user with a thoracic strap that is fastenable with matching hook and loop fastening material.

26. A method for selectively supporting a person's neck that has been injured or has had corrective surgery comprising the following steps:

providing an anterior neck plate that has broad and contoured contact with sternum and clavicle areas of the person laterally;

providing a chin plate that is extended upward and forward from the anterior neck plate and has a size, shape and contour to support the person's head from proximately under the person's mandible;

providing a posterior neck plate that has broad and contoured contact with opposite-side top and rear areas of the person's shoulders and has a back base that is extended downward from a central portion of the posterior neck plate to extend vertically over a portion of the person's upper thoracic vertebrae;

providing a head plate that is extended upward and rearward with an incline from the posterior neck plate and has a size, shape and contour to support the person's head from proximately under the person's occipital bone;

providing an adjustable-length fastener means for fastening the anterior neck plate to the posterior neck plate;

positioning the anterior neck plate over sternum and clavicle areas of the person;

positioning the posterior neck plate over opposite-side top and rear areas of the person's shoulders;

positioning the chin plate in desired contact with a bottom surface of the person's jaw;

positioning the head plate in desired contact with a bottom rear surface of the person's head;

attaching the anterior neck plate to the posterior neck plate;

adjusting fastening length of the adjustable-length fastener to adjust distance between the anterior neck plate and the posterior neck plate as desired to force the person's head upwardly with the incline of the head plate from the posterior neck plate and thereby to support the person's neck selectively upwardly from a base of a cervical-thoracic brace that has a posterior neck plate resting on the person's shoulders and has an anterior neck plate forced against a sternum and clavicle area of the person in opposition to the back base that is forced against the person's upper thoracic vertebrae;

fastening the adjustable-length fastener;

positioning a rigid thoracic bar intermediate the chin plate and a chest plate that is strapped to the person;

adjusting length of the rigid thoracic bar intermediate the chin plate and the chest plate for a desired vertical orientation of the person's head; and affixing the rigid thoracic bar to the chest plate.

* * * * *